United States Patent
Engmark et al.

(10) Patent No.: US 8,295,930 B2
(45) Date of Patent: Oct. 23, 2012

(54) MEDICAL DEVICE HAVING RESISTANCE WELDED CONNECTIONS

(75) Inventors: David B. Engmark, Bethel, MN (US); Doug Morelli, Forest Lake, MN (US); Hui Jin, Shoreview, MN (US); David M. Johnson, Ham Lake, MN (US); Mathieu K. Horié, Vaud (FR); Iryna Levina, Blaine, MN (US); Dominique Piguet, Epalinges (CH)

(73) Assignee: Medtronic, Inc., Minneapolis, MN (US)

( * ) Notice: Subject to any disclaimer, the term of this patent is extended or adjusted under 35 U.S.C. 154(b) by 491 days.

(21) Appl. No.: 12/570,411

(22) Filed: Sep. 30, 2009

(65) Prior Publication Data

US 2011/0077709 A1     Mar. 31, 2011

(51) Int. Cl.
*A61N 1/375* (2006.01)
(52) U.S. Cl. .......................................... 607/37
(58) Field of Classification Search ............ 607/36, 607/37
See application file for complete search history.

(56) References Cited

U.S. PATENT DOCUMENTS

| | | | |
|---|---|---|---|
| 5,358,514 A | 10/1994 | Schulman et al. |
| 5,545,189 A | 8/1996 | Fayram |
| 6,721,602 B2 | 4/2004 | Engmark et al. |
| 2003/0040780 A1* | 2/2003 | Haeg et al. ................ 607/36 |
| 2004/0173835 A1 | 9/2004 | Schmidt et al. |
| 2005/0007718 A1 | 1/2005 | Stevenson et al. |
| 2005/0113896 A1 | 5/2005 | Pavlik et al. |
| 2006/0018083 A1 | 1/2006 | Schmidt |
| 2010/0076533 A1 | 3/2010 | Dar et al. |

FOREIGN PATENT DOCUMENTS

| | | |
|---|---|---|
| EP | 2153868 A1 | 2/2010 |
| WO | 2004009178 A1 | 1/2004 |

OTHER PUBLICATIONS (PCT/US2010/050168) PCT Notification of Transmittal of the International Search Report and the Written Opinion of the International Searching Authority, Mailed Dec. 6, 2010, 10 pages.

* cited by examiner

*Primary Examiner* — Eric D. Bertram (57) ABSTRACT

A medical device is electrically connected to a biological tissue for transmission of an electrical signal between the medical device and the biological tissue. The medical device includes a housing assembly and a control circuit assembly that controls the electrical signal. The control circuit assembly is enclosed within the housing assembly, and the control circuit assembly includes an electrically conductive terminal. The device further includes an electrical component at least partially enclosed within the housing assembly. The electrical component has a connecting member that electrically connects the electrical component to the control circuit assembly. The connecting member is resistance welded and bonded directly to the electrically conductive terminal of the control circuit assembly.

15 Claims, 6 Drawing Sheets

MEDICAL DEVICE HAVING RESISTANCE WELDED CONNECTIONS

FIELD

The present disclosure relates to a medical device, and in particular, a medical device having resistance welded connections.

INTRODUCTION

Several medical devices have been designed to be in electrical communication with biological tissue for maintaining proper function of the biological tissue, for providing therapies, for detecting a condition of the biological tissue, and the like. For instance, implantable medical devices (IMDs), such as implantable pulse generators (IPGs) and implantable cardioverter-defibrillators (ICDs), often include an elongate, flexible lead having one end operatively coupled to cardiac tissue and an opposite end operatively coupled to a generator. The generator can include a control circuit assembly and a power source for providing power to the control circuit assembly. The control circuit assembly can control the electrical signal transmitted to the cardiac tissue. These devices can also include sensors for detecting blood pressure and the like, and the sensor can transmit a signal to the control circuit assembly to affect the electrical signal transmitted to the cardiac tissue.

Other medical devices, such as neural probes, can include one or more electrodes that are electrically connected to biological material, such as brain tissue, and a control circuit assembly. The control assembly can control electrical signals transmitted between the biological material and the device.

The following discloses a medical device that is manufactured in a way that reduces the size of the device. The manufacturing method can also reduce costs because fewer parts are needed and because the manufacturing can be completed more quickly and efficiently.

SUMMARY

This section provides a general summary of the disclosure, and is not a comprehensive disclosure of its full scope or all of its features.

A medical device is disclosed that is electrically connected to a biological tissue for transmission of an electrical signal between the medical device and the biological tissue. The medical device includes a housing assembly and a control circuit assembly that controls the electrical signal. The control circuit assembly is enclosed within the housing assembly, and the control circuit assembly includes an electrically conductive terminal. The device further includes an electrical component at least partially enclosed within the housing assembly. The electrical component has a connecting member that electrically connects the electrical component to the control circuit assembly. The connecting member is resistance welded and bonded directly to the electrically conductive terminal of the control circuit assembly.

A method of assembling a medical device that is electrically connected to biological tissue for transmission of an electrical signal between the medical device and the biological tissue is also disclosed. The method includes providing a control circuit assembly that controls the electrical signal. The control circuit assembly includes an electrically conductive terminal. The method further includes providing an electrical component having a connecting member and abutting the connecting member against the electrically conductive terminal. Furthermore, the method includes resistance welding the connecting member to the electrically conductive terminal to electrically and mechanically connect connecting member to the electrically conductive terminal directly.

Moreover, a cardiac device that delivers an electrical signal to a cardiac tissue is disclosed. The cardiac device includes a flexible lead that is operably coupled to the cardiac tissue to deliver the electrical signal to the cardiac tissue and a generator that is operably coupled to the flexible lead. The generator generates the electrical signal that is delivered to the cardiac tissue via the flexible lead. The generator includes a housing assembly and a control circuit assembly that controls the electrical signal delivered to the biological tissue. The control circuit assembly is enclosed within the housing assembly, and the control circuit assembly includes a substrate, a battery terminal with a first and second portion disposed on opposite sides of the substrate, a capacitor terminal with a first and second portion disposed on opposite sides of the substrate, and a feed through terminal with a first and second portion disposed on opposite sides of the substrate. Each of the battery terminal, the capacitor terminal, and the feed through terminal includes a via that extends through the substrate and the respective pairs of first and second portions to electrically and thermally connect the respective pairs of first and second portions. The generator further includes a battery enclosed within the housing assembly, and the battery includes a connecting member resistance welded to the battery terminal to be in direct electrical connection with the battery terminal. The generator also includes a capacitor enclosed within the housing assembly, and the capacitor includes a connecting member resistance welded to the capacitor terminal to be in direct electrical connection with the capacitor terminal. Moreover, the generator includes a feed through wire that extends from an interior of the housing assembly to an exterior of the housing assembly to operably connect the control circuit assembly to the flexible lead, and the feed through wire is resistance welded to the feed through terminal to be in direct electrical connection with the feed through terminal.

Further areas of applicability will become apparent from the description provided herein. The description and specific exemplary embodiments in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Exemplary embodiments will now be described more fully with reference to the accompanying drawings.

Figure 1:
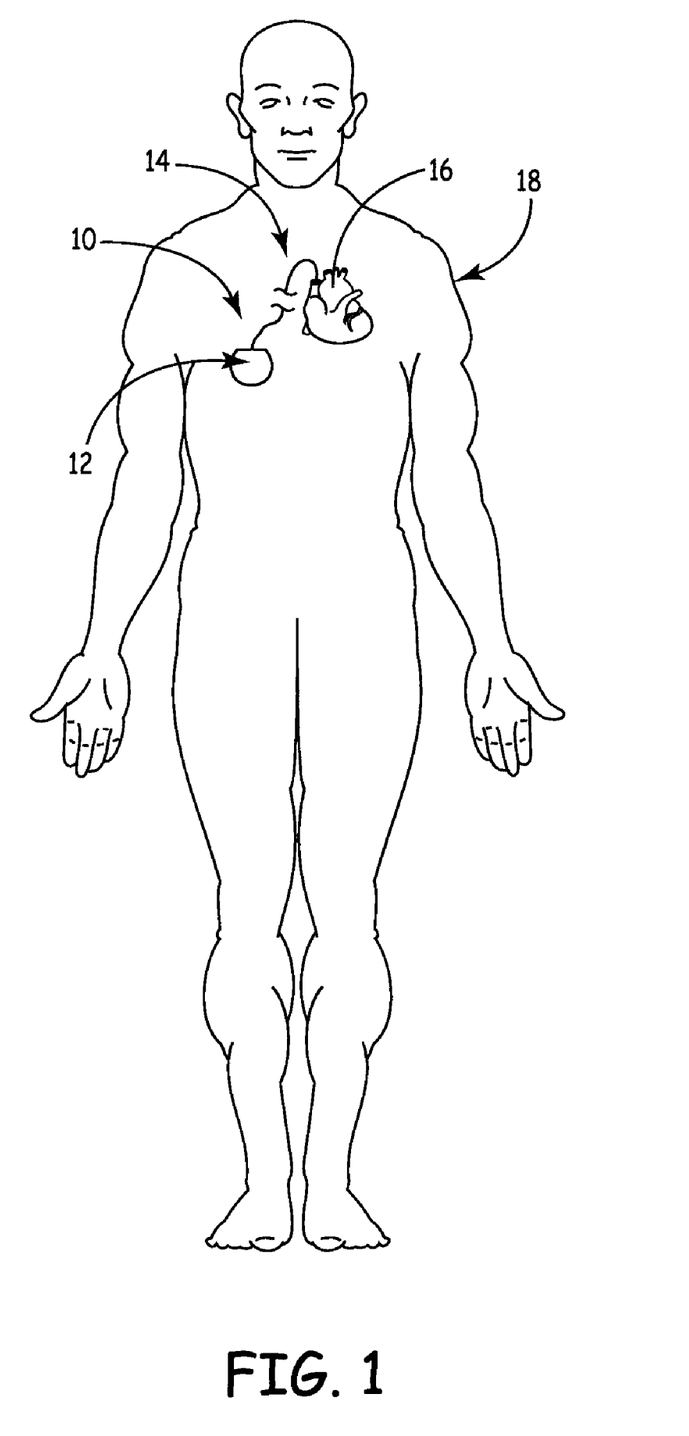
FIG. 1 is a schematic view of a medical device shown implanted within a patient.

Referring initially to FIG. 1, a medical device 10 is illustrated according to various teachings of the present disclosure. The medical device 10 can be electrically connected to biological tissue for transmission of electrical signals between the medical device 10 and the biological tissue as will be discussed in greater detail below.

The medical device 10 can be of any suitable type, and in some embodiments, the medical device 10 can be an implantable cardiac device, such as an implantable pulse generator (IPG) or an implantable cardioverter-defibrillator (ICD). As such, the medical device 10 can include a generator 12 and a flexible lead 14 that are each implanted within a patient 18. The flexible lead 14 can be elongate and flexible and can include one or more electrically conductive wires that are encased in an electrical insulator. The lead 14 can be operably coupled to and can extend through the patient 18 between the generator 12 and cardiac tissue 16.

The generator 12 can be implanted within any suitable location within the patient 18. For instance, the generator 12 can be implanted within a cavity in the chest of the patient 18. The generator 12 can generate electrical signals (i.e., pacing or defibrillation signals) that are transmitted to the cardiac tissue 16 via the lead 14. For instance, the generator 12 can generate an electrical cardiac signal to stimulate the cardiac tissue 16 and to thereby maintain a predetermined heart beat. Also, in some embodiments, the generator 12 can receive and process electrical signals that are transmitted to the generator 12 via the lead 14. For instance, the lead 14 can include a sensor (not shown) that detects a characteristic of the cardiac tissue 16 (e.g., blood pressure), a signal from the sensor can be transmitted to the generator 12 via the lead 14, and the generator 12 can process and control this signal for various purposes.

It will be appreciated that the medical device 10 can be of any suitable type, including those other than cardiac devices. For instance, the medical device 10 can be a neural device for providing electrical signals to a nerve or for any other suitable neural application. In still other embodiments, the medical device 10 can be a pressure sensor (e.g., for measuring blood pressure).

Figure 2:
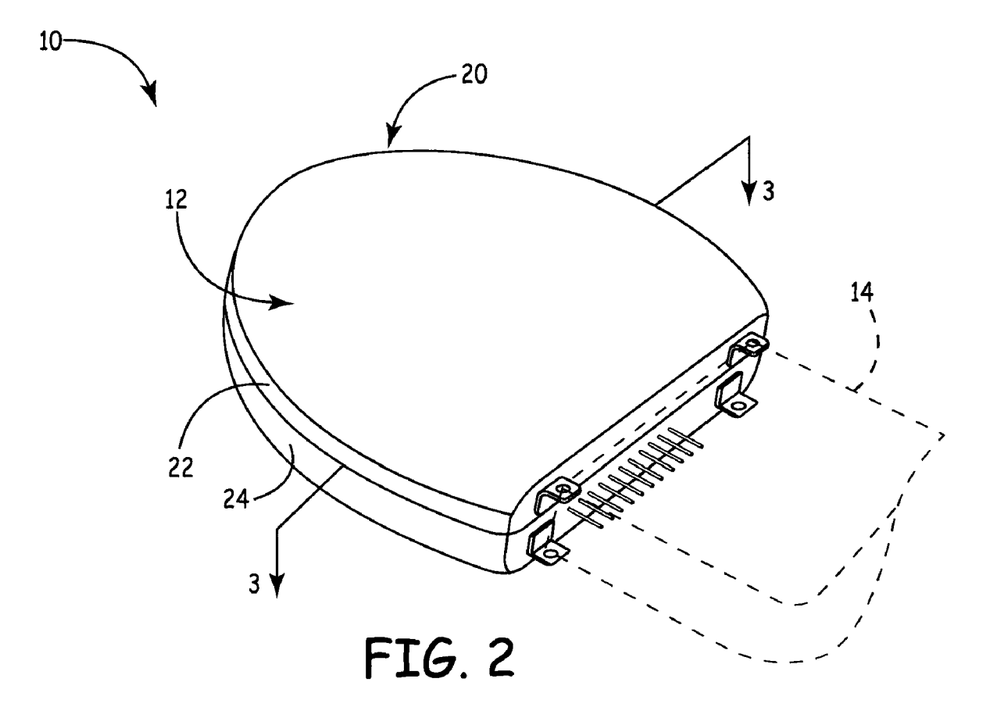
FIG. 2 is a perspective view of a generator of the medical device of FIG. 1.
Figure 3:
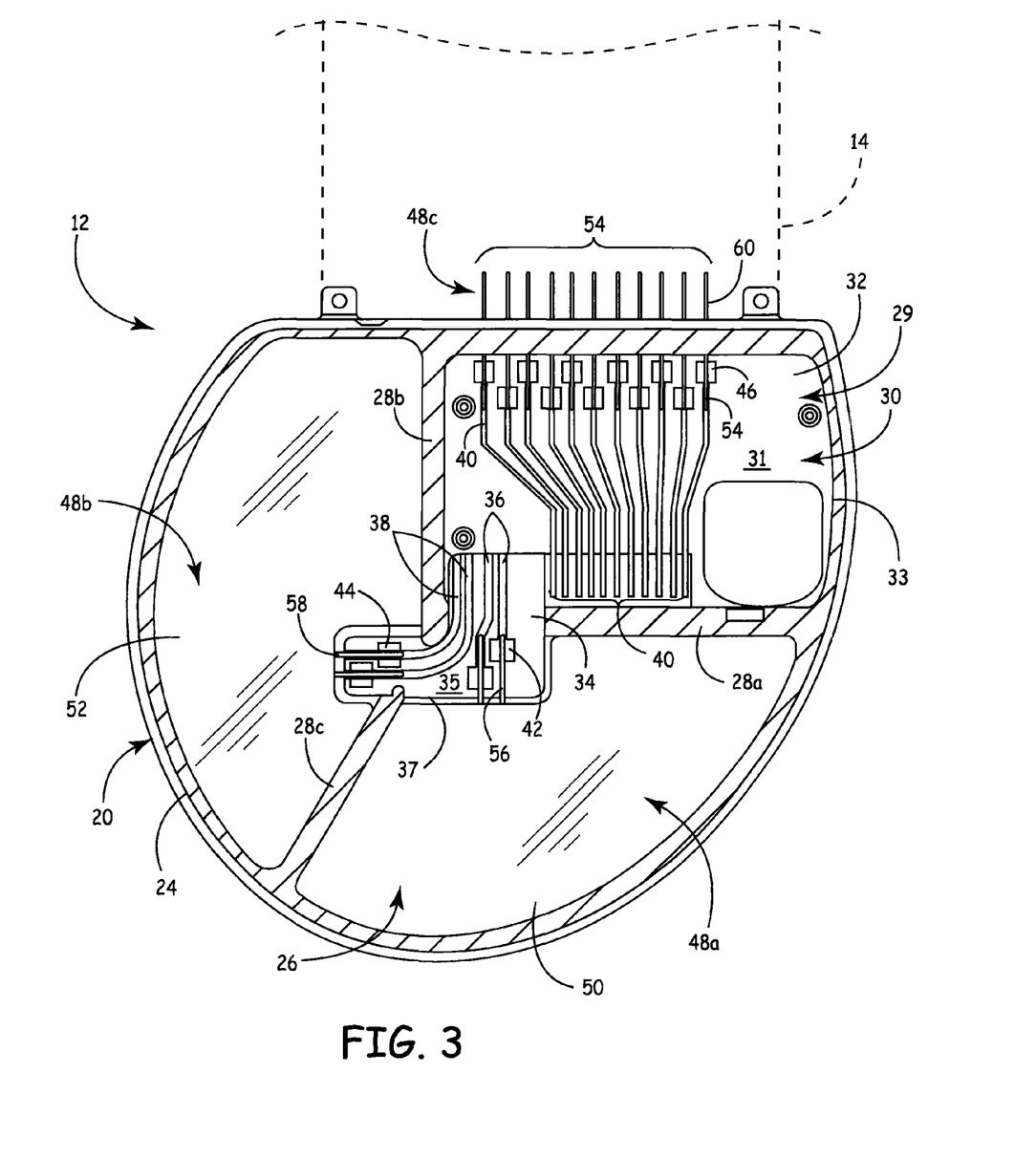
FIG. 3 is a section view of the generator of FIG. 2 taken along the line 3-3 of FIG. 2.

Referring now to FIGS. 2 and 3, the generator 12 will be discussed in greater detail. As shown, the generator 12 can include a housing assembly 20 that can at least partially encase and enclose certain components of the generator 12. As shown in FIG. 2, the housing assembly 20 can include a first portion 22 and a second portion 24. The first and second portions 22, 24 can each be made of rigid material, such as titanium. The first and second portions 22, 24 can be coupled together (e.g., via welding) and can define an internal cavity 26 (FIG. 3) therebetween. The first and/or second portions 22, 24 can also include a plurality of internal walls 28a, 28b, 28c that separate the cavity 26.

Moreover, as shown in FIG. 3, the generator 12 can include a control circuit assembly 30. The control circuit assembly 30 can be enclosed within the housing assembly 20 between two of the walls 28a, 28b. The control circuit assembly 30 can control the electrical signal transmitted between the generator 12 and the cardiac tissue 16 of the patient 18.

The control circuit assembly 30 can include one or more integrated circuits 29 that include various electrical components (e.g., amplifiers, resistors, electrical wiring, etc.) for controlling the electrical signal generated by the generator 12.

The control circuit assembly 30 can also include a rigid substrate 32 having a first surface 31 and a second surface 33. The first surface 31 (e.g., top surface) can be opposite the second surface 33 (e.g., bottom surface). The rigid substrate 32 can be made out of rigid material, such as epoxide resin or flame retardant 4 (i.e., FR4), and can be included in a circuit board of the control circuit assembly 30. The control circuit assembly 30 can further include a flexible substrate 34 having a first surface 35 and a second surface 37. The first surface 35 (e.g., top surface) can be opposite the second surface 37 (e.g., bottom surface). The flexible substrate 34 can be made out of a flexible material, such as a flexible sheet of polyimide or other polymeric material, and can be included in a flexible printed circuit board of the control circuit assembly 30. The flexible substrate 34 can be mechanically coupled to the rigid substrate 32, and electrical components on the flexible substrate 34 can be electrically coupled to respective electrical components on the rigid substrate 32 as will be discussed. It will be appreciated that the control circuit assembly 30 can include just one of the rigid and flexible substrates 32, 34 without departing from the scope of the present disclosure.

The control circuit assembly 30 can further include a plurality of first traces 36, a plurality of second traces 38, and a plurality of third traces 40. Each of the first, second, and third traces 36, 38, 40 can be elongate in shape and can be made out of electrically conductive material, such as copper, nickel, gold, or alloys thereof. As shown in FIG. 3, the control circuit assembly 30 can include two first traces 36 that are embedded in the flexible substrate 34, and each of the first traces 36 can be exposed from the first surface 35 of the substrate 34. Moreover, as shown in FIG. 3, the control circuit assembly 30 can include two second traces 38 that are embedded in the flexible substrate 34, and each of the second traces 38 can be exposed from the first surface 35 of the substrate 34. Also, the control circuit assembly 30 can include eleven third traces 40 that are embedded in the rigid substrate 32, and each of the third traces 40 can be exposed from the first surface 31 of the substrate 32.

It will be appreciated that the traces 36, 38, 40 can be electrically connected to various electrical components (e.g., amplifiers, resistors, etc.) mounted on either the flexible or rigid substrates 32, 34 of the control circuit assembly 30. Also, it will be appreciated that the control circuit assembly 30 can include any suitable number of traces 36, 38, 40 without departing from the scope of the present disclosure.

Additionally, the control circuit assembly 30 can include a plurality of electrically conductive battery terminals 42, a plurality of electrically conductive capacitor terminals 44, and a plurality of electrically conductive feed through terminals 46. The battery terminals 42 can each be electrically connected to respective ones of the first traces 36, the capacitor terminals 44 can each be electrically connected to respective ones of the second traces 38, and the feed through terminals 46 can each be electrically connected to respective ones of the third traces 40.

The generator 12 can also include one or more electrical components 48a, 48b, 48c that are at least partially enclosed within the housing assembly 20. The electrical components 48a, 48b, 48c can be electrically and operably connected to the control circuit assembly 30 via the terminals 42, 44, 46 as will be discussed in greater detail below.

The electrical components 48a, 48b, 48c can be of any suitable type for allowing proper operation of the generator 12. For instance, the electrical components 48a, 48b, 48c can include a battery 50 that supplies power to the control circuit assembly 30, a capacitor 52 that discharges to deliver electrical signals to the cardiac tissue 16, and a plurality of feed through wires 54 that each extend from inside the housing assembly 20 to outside the housing assembly 20 to electrically connect to the lead 14 (shown in phantom in FIGS. 2 and 3). In other embodiments, the electrical components 48a, 48b, 48c can include an alarm system (not shown) that triggers an alarm (e.g., audible or tactile alarm) when blood pressure of the patient 18 is detected to be abnormal.

The battery 50 can include plural connecting members 56 (e.g., a positive and a negative terminal), the capacitor 52 can include plural connecting members 58 (e.g., a positive and a negative terminal), and the feed through wires 54 can include plural (e.g., eleven) connecting members 60. The connecting members 56, 58, 60 can each be elongate, rigid wires with a round cross section made out of electrically conductive material, such as niobium, titanium, tantalum, etc.

Figure 7:
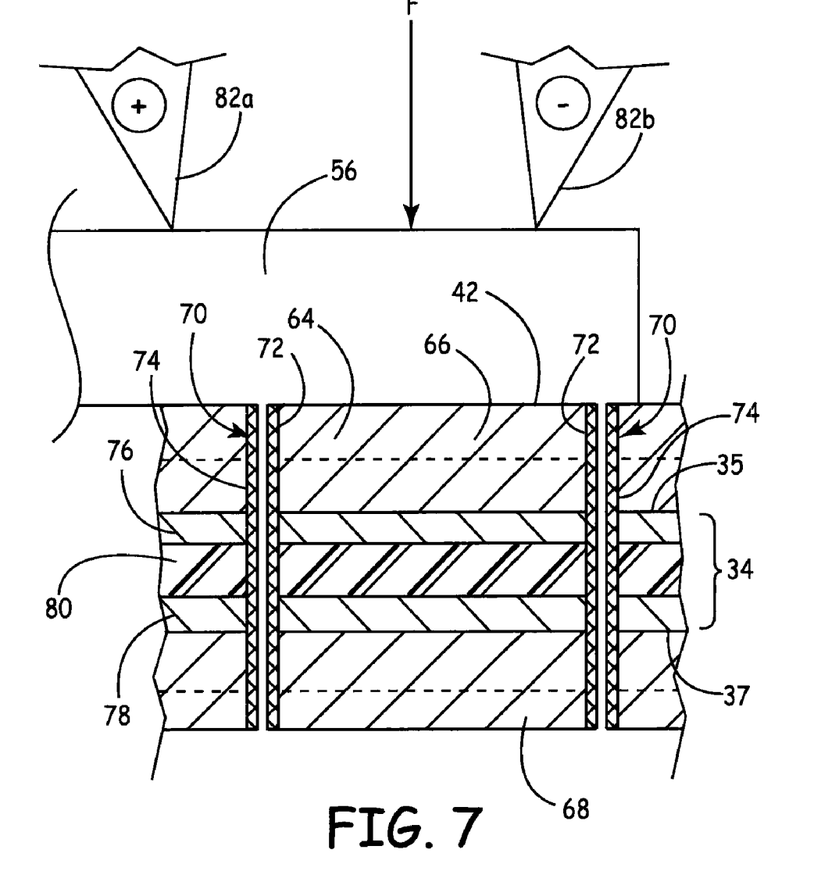
FIG. 7 is a section view of the integrated circuit board of the generator of FIG. 2 shown while a connecting member is resistance welded to the terminal.

The connecting members 56 of the battery 50 can each abut and directly connect (e.g., mechanically and electrically) to respective ones of the battery terminals 42 (see FIG. 7). Similarly, the connecting members 58 of the capacitor 52 can each abut and directly connect (e.g., mechanically and electrically) to respective ones of the capacitor terminals 44. Furthermore, the connecting members 60 of the feed through wires 54 can each abut and directly connect (e.g., mechanically and electrically) to respective ones of the feed through terminals 46. As such, the battery 50, the capacitor 52, and the feed through wires 54 can be electrically connected to the respective terminals 42, 44, 46 and to the control circuit assembly 30.

In some embodiments, one or more of the connecting members 56, 58, 60 can be connected to the respective terminal 42, 44, 46 via a welding process as will be discussed in greater detail below. For instance, the connecting members 56, 58, 60 can be connected to the respective terminal 42, 44, 46 via a resistance welding process, which is illustrated in FIG. 7. It will be understood that resistance welding is a process in which surfaces (e.g., the abutting surfaces of the connecting members 56, 58, 60 and the respective terminals 42, 44, 46) bond due to heat that is generated when a welding current flows between the surfaces. More specifically, electrical resistance is generated between the abutting surfaces, increasing the temperature enough to bond the surfaces. As such, electrical connection can be ensured, and yet the generator 12 can be relatively compact. Also, this welding process can be completed efficiently, and manufacture of the generator 12 can be completed in a less expensive manner.

Figure 4:
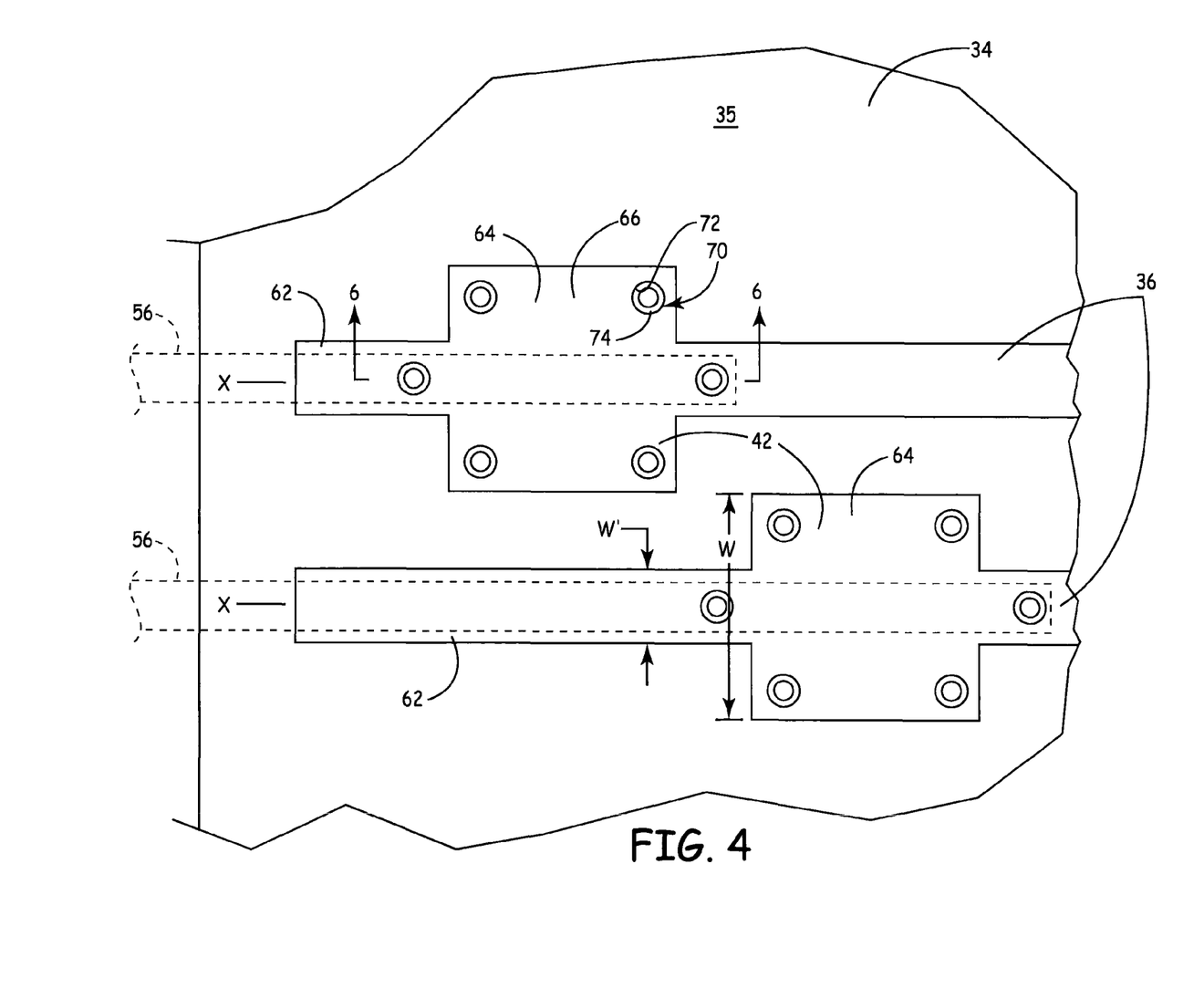
FIG. 4 is a detail view of terminals of an integrated circuit board of the generator of FIG. 2.

As shown in FIG. 4, each of the terminals 42, 44, 46 can include an elongate portion 62 and an enlarged portion 64. (For purposes of clarity, only two of the battery terminals 42 are shown; however, it will be understood that all of the terminals 42, 44, 46 can be similarly constructed.) The elongate portion 62 can be elongate and can extend along a respective longitudinal axis X to terminate adjacent the edge of the substrate 34. The enlarged portion 64 can be rectangular (e.g., square) and connected (e.g., integrally connected) to the elongate portion 62. The enlarged portion 64 can have a width, W, that is greater than a width, W', of the elongate portion 62. Also, the enlarged portion 64 can be bisected substantially symmetrically by the axis X. Thus, the enlarged portions 64 can have an increased surface area to thereby facilitate resistance welding of the respective connecting member 56, 58, 60 to the control circuit assembly 30.

As shown in FIG. 4, the enlarged portions 64 are spaced apart from each other in a direction substantially parallel to the axes X. In some embodiments, each enlarged portion 64 can be spaced apart in the X direction from the enlarged portion(s) 64 that are immediately adjacent. Accordingly, the terminals 42, 44, 46 can have sufficient surface area for resistance welding due to the increased surface area of the enlarged portions 64, and yet the control circuit assembly 30 can be relatively compact because the enlarged portions 64 are spaced apart (i.e., staggered) in the X direction.

Furthermore, as shown in FIG. 7, the terminals 42 can include a first portion 66 and a second portion 68. (For clarity, only one terminal 42 is shown in FIG. 7, but it will be appreciated that each of the terminals 42, 44, 46 can be similarly constructed.) The first portion 66 can be disposed on the first surface 35 of the substrate 34, and the second portion 68 can be disposed on the second (opposite) surface 37 of the substrate 34. The first and second portions 66, 68 can be similarly shaped. For instance, the first and second portions 66, 68 can have the same rectangular shape of the enlarged portion 64 shown in FIG. 4. Moreover, the first and second portions 66, 68 can overlap each other as shown in FIG. 7. As will be discussed in greater detail, the first and second portions 66, 68 can be electrically and thermally connected, thereby allowing the second portion 68 to act as a heat sink to the first portion 66. As such, the first and second portions 66, 68 cooperate to provide a relatively large volume of material such that the terminal 42 can better withstand the heat of a resistance welding process when connecting the connecting member 56 of the battery 50. Despite having a relatively large volume, the terminals 42 can be relatively compact because the first and second portions 66, 68 are located on opposite sides of the substrate 34. It will be appreciated that each terminal 42, 44, 46 can include a first and second portion 66, 68 similar to the embodiments of FIG. 7 for ensuring proper resistance welding when connecting the battery 50, the capacitor 52, and the feed through wires 54.

Figure 5:
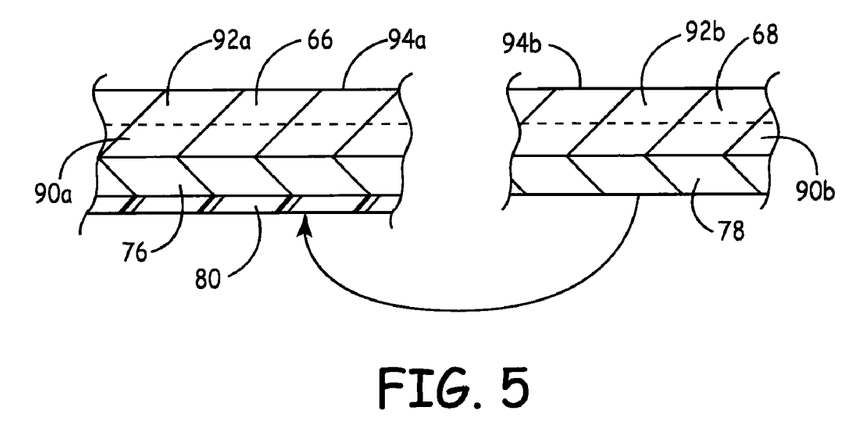
FIG. 5 is a section view of portions of the integrated circuit board of the generator of FIG. 2 shown in the process of being assembled.

In some embodiments shown in FIG. 7, the substrate 34 can have a first layer 76 and a second layer 78 of similar materials. The first layer 76 can be joined to the second layer 78, for instance via an adhesive 80. During manufacture of the substrate 34 (as represented in FIG. 5), the first portion 66 of the terminal 42 can be formed on the first layer 76 of the substrate 34. For instance, a base layer 90a (e.g., approximately 35 micron-thick rolled annealed copper) can be deposited on the first layer 76. Then, an upper layer 92a (e.g., 35 micron-thick copper) can be deposited (e.g., by electroplating) on the base layer 90a. Additional upper layers 94a, such as 4 micron-thick nickel and 1 micron-thick gold (with the nickel being layered between the gold and copper), can be applied onto the upper layer 92a as well. Base layer 90b and upper layers 92b, 94b of the second portion 68 of the terminal 42 can also be formed on the second layer 78 of the substrate 34. Then, the first and second layers 76, 78 can be subsequently joined (e.g., with adhesive 80) such that the first and second portions 66, 68 overlap. In other embodiments, the first and second layers 76, 78 can be joined together before the first and second portions 66, 68 are formed on the substrate 34.

Figure 6:
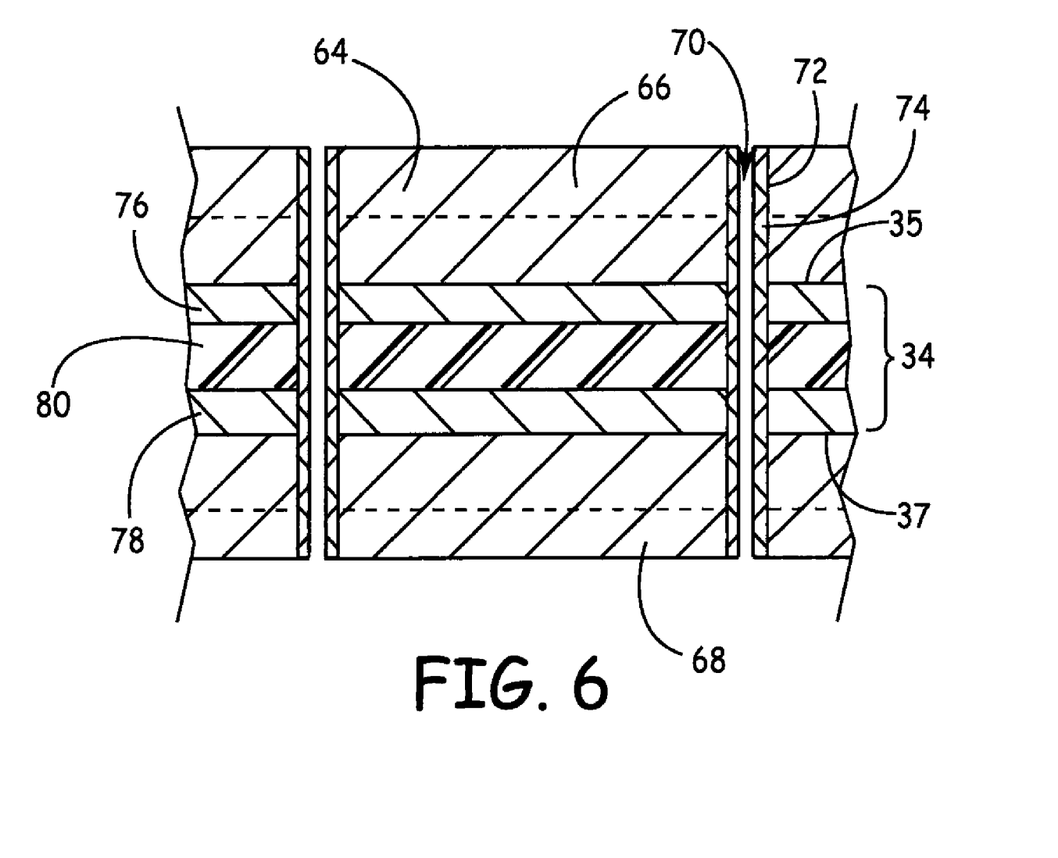
FIG. 6 is a section view of the integrated circuit board of the generator of FIG. 2 taken along the line 6-6 of FIG. 4.

Also, as shown in FIGS. 6 and 7, the terminals 42 can include one or more vias 70. Each via 70 can include a through hole 72 that extends through the first portion 66, the first layer 76, the adhesive 80, the second layer 78, and the second portion 68. Each via 70 can also include a conductive plug member 74 that at least partially fills the respective through hole 72. For instance, the plug member 74 can cover the inner surface of the through hole 72 and can extend continuously from the first portion 66 to the second portion 68. As shown in FIG. 4, the vias 70 can be formed adjacent each corner and on both sides of the enlarged portion 64 of the terminal 42. The plug member 74 can be made out of electrically conductive material, such as nickel, copper, gold or an alloy thereof. During manufacture, the through holes 72 can be formed by punching, drilling, or by any other suitable process after the first and second portions 66, 68 are formed and the first and second layers 76, 78 have been joined. Then, the material of the plug members 74 can be provided in the through holes 72. As such, the plug members 74 electrically and thermally connect the first and second portions 66, 68 of the terminal 42.

It will be appreciated that the rigid substrate 32 can be constructed with a first and second layer similar to the first and second layers 76, 78 of the flexible substrate 34 shown in FIG. 5. Moreover, it will be appreciated that each of the terminals 42, 44, 46 can be constructed in a manner similar to that shown in FIG. 7 and described above.

Once the control circuit assembly 30 is formed as discussed above, the battery 50 can be placed such that the connecting members 56 of the battery 50 lie over and directly abut the respective enlarged portion 64 of respective battery terminal 42 (FIGS. 3 and 7). Then, a positive electrode 82a and a negative electrode 82b can contact the connecting member 56. Force (shown as "F" in FIG. 7) can be applied to the connecting member 56 from the electrodes 82a, 82b or from separate means to close any gap between the connecting member 56 and the terminal and to ensure sufficient contact between the connecting member 56 and the terminal 42. The force F is directed toward the terminal 42. It will be appreciated that force F could also be applied from the terminal 42 toward the connecting member 56. Next, current can flow between the electrodes 82a, 82b, and electrical resistance between the connecting member 56 and the first portion 66 of the terminal 42 can generate enough heat to bond (i.e., resistance weld) the connecting member 56 to the terminal 42.

Figure 8:
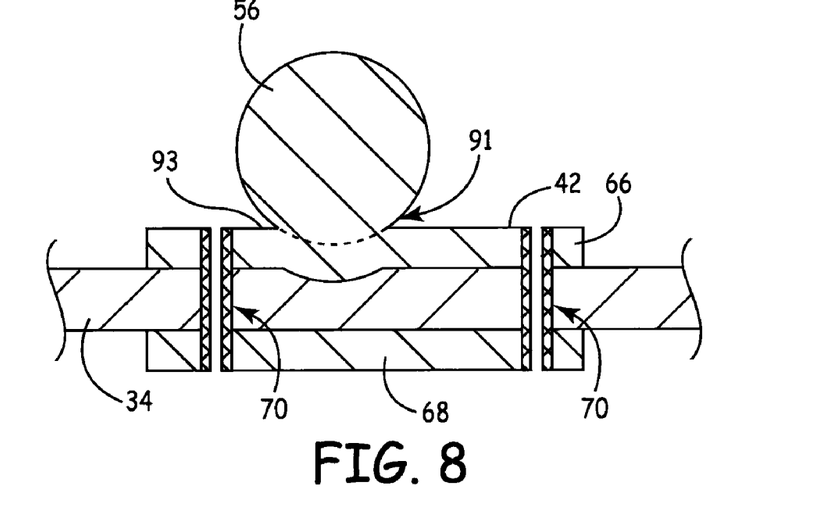
FIG. 8 is a section view of the integrated circuit board of the generator of FIG. 2 shown with the connecting member is resistance welded to the terminal.

Once the connecting member 56 has been bonded to the terminal 42 (FIG. 8), the connecting member 56 is mechanically and electrically connected. As shown in FIG. 8, the bond 91 is continuous between the connecting member and the terminal 42. Furthermore, the substrate 34 can be compressed slightly underneath the bond 91 due to the resistance welding process so as to define a concave contour 93. As such, the connection is very robust. Also, this direct connection can be more compact because separate, bulky connectors are not used to establish the connection between the connecting member 56 and the terminal 42. Furthermore, this type of assembly can be completed efficiently and less expensively because separate connectors are unnecessary.

In some embodiments, the force F applied is between approximately 4 and 5 lbf. Also, in some embodiments, there is a gap of between approximately 20 and 30 mils between the connecting members 56 and the respective terminals 42 before the resistance welding process begins. Furthermore, in some embodiments, approximately 520 to 540 amps of current are applied by the electrodes 82a, 82b during the resistance welding process. Additionally, the current is applied for between approximately 2 and 3 milliseconds.

It will be appreciated that the terminal 42 is unlikely to be vaporized due to the heat of the welding process. This is because the terminal 42 includes a relatively large volume of material, due to the increased surface area of the enlarged portion 64, and due to the increased volume of the first and second portions 66, 68 on opposite surfaces 35, 37 of the substrate 34.

It will also be appreciated that the connecting members 58 of the capacitor 52 can be connected to the respective capacitor terminals 44 via resistance welding in the manner described above. Likewise, it will be appreciated that the connecting members 60 of the feed through wires 54 can be connected to the respective feed through terminals 46 via resistance welding in the manner described above. Once these electrical connections have been established, the first and second portions 22, 24 of the housing assembly 20 can be coupled to enclose the control circuit assembly 30, the battery 50, and the capacitor 52, and such that the feed through wires 54 extend out of the housing assembly 20.

Accordingly, the battery 50, capacitor 52, feed through wires 54, and/or other electrical components of the generator 12 can be electrically connected to the control circuit assembly 30 through a robust resistance welding process. However, the generator 12 can remain relatively compact and relatively inexpensive to manufacture.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Exemplary embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent,"

etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A medical device that is electrically connected to a biological tissue for transmission of an electrical signal between the medical device and the biological tissue, the medical device comprising:
    a housing assembly;
    a control circuit assembly that controls the electrical signal, the control circuit assembly enclosed within the housing assembly, and the control circuit assembly including an electrically conductive terminal and wherein the electrically conductive terminal includes first and second electrically conductive portions disposed on opposite sides of a substrate and at least one through hole through the first portion, the substrate, and the second portion, and a conductive member in the through hole that electrically and thermally connects the first and second portions; and
    an electrical component at least partially enclosed within the housing assembly, the electrical component having a connecting member that electrically connects the electrical component to the control circuit assembly, the connecting member being resistance welded and bonded directly to the electrically conductive terminal of the control circuit assembly.

2. The medical device of claim 1, wherein the electrical component is at least one of a battery that supplies power to the control circuit assembly, a capacitor that discharges to deliver the electrical signal to the biological tissue, and a feed through wire that extends from inside the housing assembly to outside the housing assembly.

3. The medical device of claim 1, wherein the electrically conductive terminal includes an elongate portion having a longitudinal axis and an enlarged portion that has a width that is greater than a width of the elongate portion.

4. The medical device of claim 3, comprising a first electrically conductive terminal and a second electrically conductive terminal, each with an elongate portion, a longitudinal axis, and an enlarged portion, wherein the enlarged portion of the first electrically conductive terminal is spaced apart from the enlarged portion of the second electrically conductive terminal in a direction substantially parallel to the respective longitudinal axes.

5. The medical device of claim 3, wherein the enlarged portion is bisected substantially symmetrically by the longitudinal axis.

6. The medical device of claim 1, wherein the control circuit assembly includes at least one of a flexible substrate and a rigid substrate.

7. A method of assembling a medical device that is configured to be electrically connected to biological tissue for transmission of an electrical signal between the medical device and the biological tissue, the method comprising:
    providing a control circuit assembly that controls the electrical signal, the control circuit assembly including an electrically conductive terminal, the electrically conductive terminal having first and second electrically conductive portions disposed on opposite sides of a substrate and at least one through hole through the first portion, the substrate, and the second portion, and a conductive member in the through hole that electrically and thermally connects the first and second portions;
    providing an electrical component having a connecting member;
    abutting the connecting member against the electrically conductive terminal; and
    resistance welding the connecting member to the electrically conductive terminal to electrically and mechanically connect connecting member to the electrically conductive terminal directly.

8. The method of claim 7, wherein the electrical component is at least one of a battery that supplies power to the control circuit assembly, a capacitor that discharges to deliver the electrical signal to the biological tissue, and a feed through wire that extends from inside a housing assembly to outside the housing assembly, the housing assembly at least partially enclosing the control circuit assembly and the electrical component.

9. The method of claim 7, further comprising at least partially enclosing the control circuit assembly and the electrical component within a housing assembly.

10. The method of claim 7, wherein providing the control circuit assembly further comprises attaching a first layer of the substrate to a second layer of the substrate such that the first side and the first portion face away from the second side and the second portion.

11. The method of claim 7, wherein providing the control circuit assembly further includes providing a flexible substrate of the control circuit assembly and a rigid substrate of the control circuit assembly, each including a respective electrically conductive terminal.

12. The method of claim 7, further comprising applying a pressure to one of the connecting member and the electrically conductive terminal directed toward the other of the connecting member an the electrically conductive terminal during the resistance welding.

13. The method of claim 7, wherein resistance welding the connecting member to the electrically conductive terminal includes applying between approximately 520 to 540 amps of current to the connecting member and the electrically conductive terminal.

14. The method of claim 13, wherein resistance welding includes applying the current for between approximately 2 and 3 milliseconds.

15. A cardiac device that delivers an electrical signal to a cardiac tissue, the cardiac device comprising:

a flexible lead that is operably coupled to the cardiac tissue to deliver the electrical signal to the cardiac tissue; and a generator that is operably coupled to the flexible lead, the generator generating the electrical signal that is delivered to the cardiac tissue via the flexible lead, the generator including:

a housing assembly;

a control circuit assembly that controls the electrical signal delivered to the biological tissue, the control circuit assembly enclosed within the housing assembly, and the control circuit assembly including a substrate, a battery terminal with a first and second portion disposed on opposite sides of the substrate, a capacitor terminal with a first and second portion disposed on opposite sides of the substrate, and a feed through terminal with a first and second portion disposed on opposite sides of the substrate, wherein each of the battery terminal, the capacitor terminal, and the feed through terminal includes a via that extends through the substrate and the respective pairs of first and second portions to electrically and thermally connect the respective pairs of first and second portions;

a battery enclosed within the housing assembly, the battery including a connecting member resistance welded to the battery terminal to be in direct electrical connection with the battery terminal;

a capacitor enclosed within the housing assembly, the capacitor including a connecting member resistance welded to the capacitor terminal to be in direct electrical connection with the capacitor terminal; and a feed through wire that extends from an interior of the housing assembly to an exterior of the housing assembly to operably connect the control circuit assembly to the flexible lead, the feed through wire resistance welded to the feed through terminal to be in direct electrical connection with the feed through terminal.

\* \* \* \* \*

UNITED STATES PATENT AND TRADEMARK OFFICE
CERTIFICATE OF CORRECTION

| | | |
|---|---|---|
| PATENT NO. | : 8,295,930 B2 | |
| APPLICATION NO. | : 12/570411 | |
| DATED | : October 23, 2012 | |
| INVENTOR(S) | : David B. Engmark et al. | |

It is certified that error appears in the above-identified patent and that said Letters Patent is hereby corrected as shown below:

Col. 10, line 56, delete "...member an the electrically..." and insert in place thereof -- member and the electrically --

Signed and Sealed this
First Day of January, 2013

David J. Kappos
*Director of the United States Patent and Trademark Office*